US00PP21894P2

(12) United States Plant Patent
Hurd

(10) Patent No.: US PP21,894 P2
(45) Date of Patent: May 3, 2011

(54) ***DIANTHUS* PLANT NAMED 'DRAGON FRUIT'**

(50) Latin Name: ***Dianthus* hybrid**
Varietal Denomination: Dragon Fruit

(75) Inventor: Kevin Hurd, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 12/462,745

(22) Filed: Aug. 7, 2009

(51) Int. Cl.
*A01H 5/00* (2006.01)

(52) U.S. Cl. ..... Plt./272

(58) Field of Classification Search ..... Plt./272
See application file for complete search history.

*Primary Examiner* — Susan B McCormick Ewoldt

(57) ABSTRACT

The new and distinct cultivar of perennial Carnation or Pinks, *Dianthus* plant named "Dragon Fruit' with fragrant highly double flowers, petals with a central fuchsia pink zone and reddish purple bar. *Dianthus* "Dragon Fruit' is tolerant of high temperatures and resists center die out.

2 Drawing Sheets

Botanical denomination: *Dianthus* hybrid.
Cultivar designation: 'Dragon Fruit'.

BACKGROUND OF THE INVENTION

The present invention relates to the new and distinct cultivar of *Dianthus* or Pinks from the genus *Dianthus* and given the cultivar name 'Dragon Fruit'. The new plant was the result of an intentional cross in May of 2006 by Kevin A. Hurd between 'Double Spotty' U.S. Plant Pat. No. 13,884 as the seed parent and 'Devon Siskin' U.S. Plant Pat. No. 14,377 (more often known as 'Raspberry Swirl') as the pollen parent. The new hybrid was first isolated from trials at a nursery in Zeeland, Mich. during the summer of 2007. *Dianthus* 'Dragon Fruit" has been asexually propagated at the same nursery in Zeeland, Mich. using traditional shoot tip cutting procedures and found to reproduce plants that are identical and exhibit all the characteristics of the original plant.

SUMMARY OF THE INVENTION

The present invention has not been evaluated under all possible environmental conditions. The phenotype may vary with variations in environment including: growing temperature, available sunlight, nutrients, water, etc. without a change in the genotype of the plant. The new plant is distinct from its parents and all other *Dianthus* known to the applicant in the following combined traits:

1. Double flowers with high petal counts.
2. Unique floral color and pattern.
3. High heat tolerance.
4. Floriferous habit.
5. Vigorous growth and excellent habit.
6. Compact, distinctly blue-green foliage.

Cultivar Comparison Table

| Cultivar | Flower color | Flower pattern | Flower size |
|---|---|---|---|
| 'Apple Slice' application No. 12/462,743 | pink | dark wine edge and rim | 4.5 cm |

-continued

Cultivar Comparison Table

| | | | |
|---|---|---|---|
| 'Black Cherry Wild' application No. 12/462,742 | burgundy | solid | 4.0 cm |
| 'Coconut Punch' application No. 12/462,744 | white | burgundy edge with white rim | 3.5 cm |
| 'Double Spotty' U.S. Plant Pat. No. 13,884 | burgundy | white picotee edge and white spots | 4.0 cm |
| 'Dragon Fruit' application No. 12/462,745 | fuchsia pink | red jagged purple bar | 3.5 cm |
| 'Pomegranate Kiss' application No. 12/462,746 | burgundy | irregular pink splashing on margin or center | 3.2 cm |
| 'Cranberry Ice' U.S. Plant Pat. No. 18,342 | pink | dark wine edge and rim | 3.3 cm |
| 'Devon Siskin' U.S. Plant Pat. No. 14,377 | light pink | magenta edge with burgundy base | 4.0 cm |
| 'Feuerhexe' (not patented) | pink | solid | 4.0 cm |
| 'Devon Xera' U.S. Plant Pat. No. 14,895 | red | crimson eye | 3.0 cm |
| Red Dwarf' U.S. Plant Pat. No. 14,437 | red | crimson eye | 3.5 cm |
| 'Sangria Splash' application No. 12/462,741 | fuchsia pink | crimson ring with pink splashing and center | 3.0 cm |
| 'Spangled Star' U.S. Plant Pat. No. 13,029 | scarlet red | small white spots and white picotee edge | 4.0 cm |

| Cultivar | Petal margin | Petal # | Plant height in flower |
|---|---|---|---|
| 'Apple Slice' application No. 12/462,743 | dark wine margin | 20 to 24 | 22 cm |
| 'Black Cherry Wild' application No. 12/462,742 | light rose margin | 16 to 20 | 22 cm |
| 'Coconut Punch' application No. 12/462,744 | reddish purple margin | 14 to 30 | 28 cm |
| 'Double Spotty' | white | 15 to | 17 to 30 cm |

-continued

Cultivar Comparison Table

| | | | |
|---|---|---|---|
| U.S. Plant Pat. No. 13,884 | | 20 | |
| 'Dragon Fruit' | self | 14 to | 20 cm |
| application No. 12/462,745 | | 22 | |
| 'Pomegranate Kiss' | irregular | 16 to | 16 cm |
| application No. 12/462,746 | pink | 22 | |
| | splashing | | |
| 'Cranberry Ice' | dark wine | 5 | 20 to 25 cm |
| U.S. Plant Pat. No. 18,342 | margin | | |
| 'Devon Siskin' | magenta | 5 | 10 cm |
| U.S. Plant Pat. No. 14,377 | edge | | |
| 'Feuerhexe' (not patented) | self | 5 | 10 to 12 cm |
| 'Devon Xera' | self | 5 | 15 to 20 cm |
| U.S. Plant Pat. No. 14,895 | | | |
| Red Dwarf' | self | 5 | 20 to 25 cm |
| U.S. Plant Pat. No. 14,437 | | | |
| 'Sangria Splash' | crimson with | 5 | 30 cm |
| application No. 12/462,741 | pink | | |
| | splashing | | |
| 'Spangled Star' | white | 5 | 17 to 22 cm |
| U.S. Plant Pat. No. 13,029 | picotee edge | | |

BRIEF DESCRIPTION OF THE DRAWINGS

The photographs of the new invention demonstrate the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
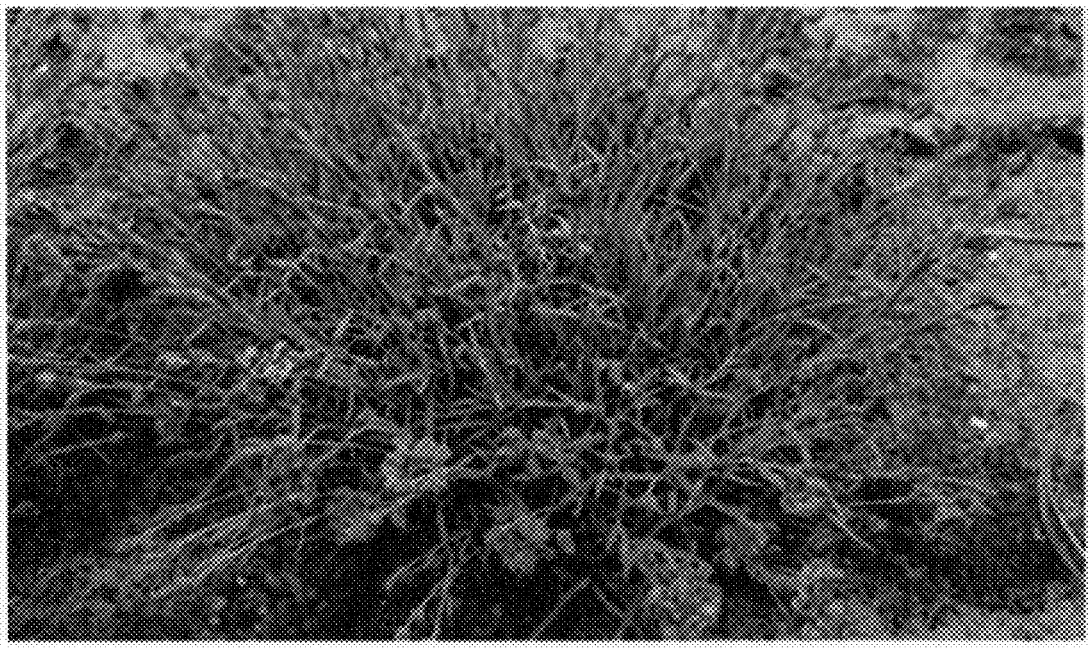
FIG. 1 shows the two-year old new plant in flower.
Figure 2:
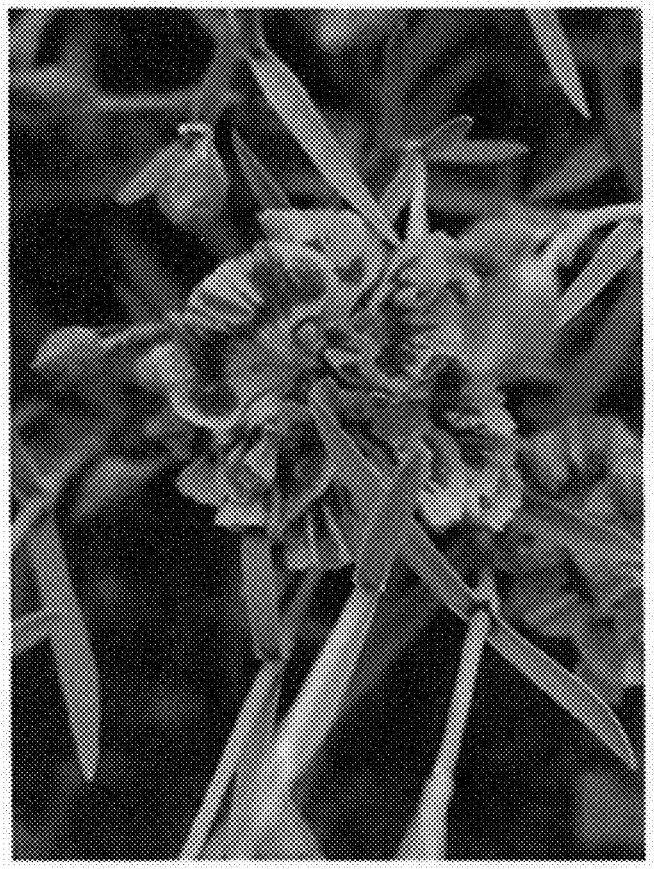
FIG. 2 shows a close-up of the flower and bud.
Figure 3:
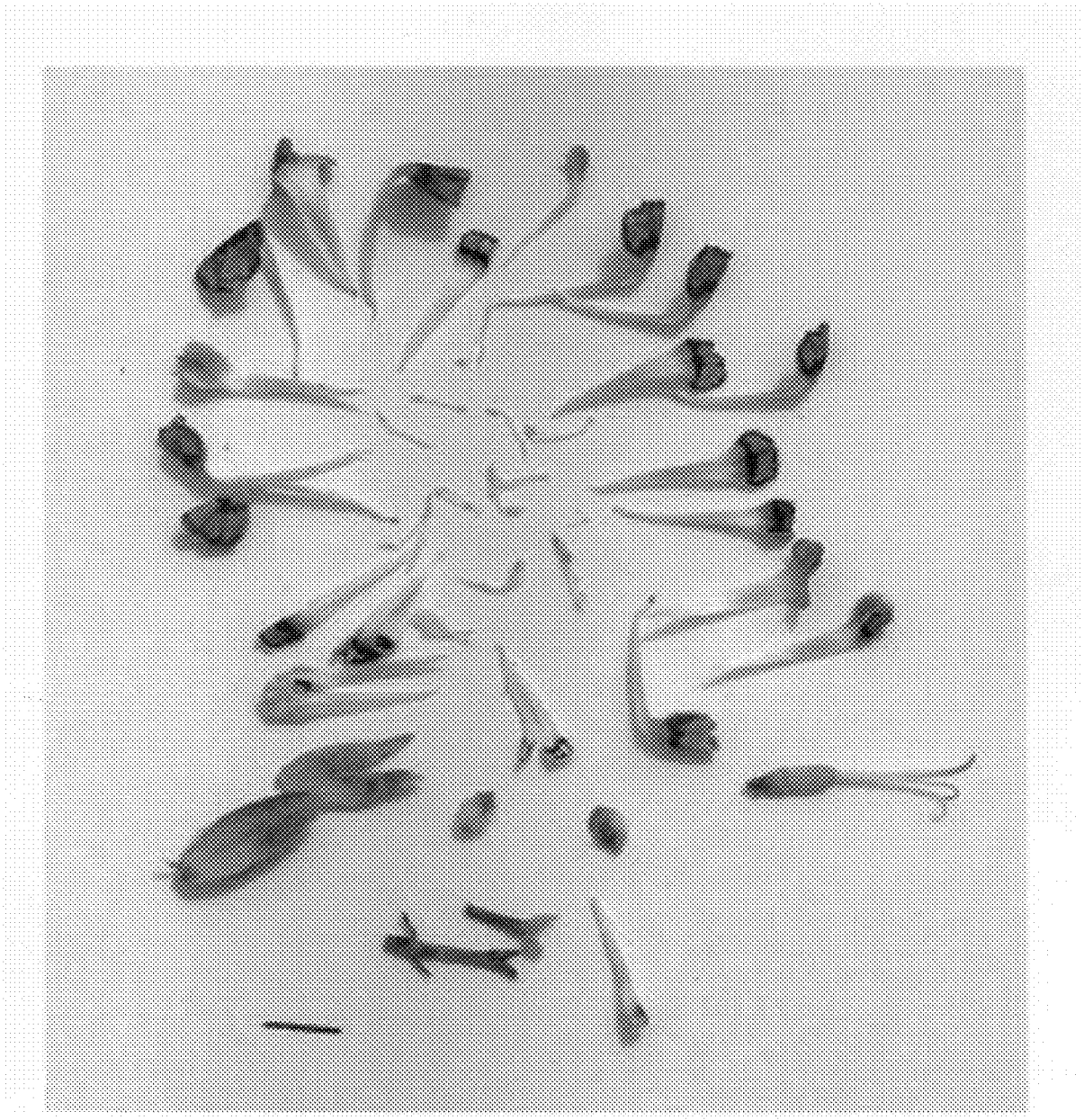
FIG. 3 shows the dissected flower of the new plant together with capsule and seeds.

The following detailed description of the new plant is based on observations of several two-year old plants in open-field, full-sun conditions in Zeeland, Mich. with supplemental watering, light additions of fertilizer and free of other plant growth regulators. All color usage is in reference to the 2001 edition of The Royal Horticultural Colour Chart except where common dictionary terms are used.

Botanical classification: *Dianthus* hybrid;

Parentage: 'Double Spotty' (female) times 'Raspberry Swirl' (male);

Plant description:

*Habit.*—Cespitose, herbaceous, evergreen perennial; stems proximally branched, erect; height of foliage about 14 cm and 30 cm across; height in flower is about 20 cm; Root system; fibrous.

Foliage:

*Leaf type.*—Simple, linear, opposite, decussate, sessile, glabrous, glaucous on adaxial and abaxial; acute apex; base decurrent, adpressed along stem and somewhat perfoliate; no fragrance detected.

*Leaf dimensions.*—About 5.5 cm long and 4 mm wide.

*Leaf color.*—Nearest RHS 122B adaxial and abaxial sides.

*Fragrance.*—None detected.

*Venation.*—Finely reticulate, coloration same as that of leaf top and bottom.

*Stems.*—Erect to arching, terete, glabrous, glaucous, proximally branching at 3 to 4 nodes.

*Stem size.*—About 20 cm long and 2 mm wide at base.

*Stem color.*—Nearest RHS 122B.

*Branching.*—Numerous from lower leaf axils; about 144 per plant.

*Nodes.*—4 mm across, RHS 138D.

*Internodes.*—4 to 5 cm apart.

Inflorescence:

*Type.*—Terminal, cymose, erect.

*Flowers per stem.*—Usually 3 to 4.

*Pedicel.*—Glaucous, glabrous, terete.

*Pedicel size.*—Usually 2 to 3 cm long and 2 mm diameter.

*Pedicel color.*—Nearest RHS 122A.

Flowers:

*Type.*—Salviform, completely double, symmetrical.

*Dimension.*—About 3.5 cm across and extending about 1.7 cm above calyx.

*Flower bud shape.*—Rhomboid to ovoid.

*Flower bud size one day prior to opening.*—About 2 cm long and 1 cm wide.

*Flower bud color.*—Glaucous, nearest RHS N138B and with anthocyanin patches between RHS 184B and RHS N186B.

*Flower period.*—Beginning late May and flowering until frost in the fall with a short 2 week rest after the initial bust.

*Flower lasting quality.*—About one week on or off the plant.

*Flower fragrance.*—Light, sweet spicy, clove-like.

Petals:

*Petals.*—14 to 22, consisting of a rounded blade or limb and a claw (enclosed completely within the calyx), obovate, apex dentate with dentations 1 to 2 mm deep, bearded with minute hairs mostly on the center of the adaxial surface, bent outwardly to nearly a ninety degree angle; adaxial limb with reddish purple jagged bar about 2 mm thick perpendicular to claw and rim of identical reddish purple or lighter 1 to 2 mm wide and 1 to 2 mm inside limb margin; abaxial side.

*Dimension.*—Variable, to 3.0 cm long including claw and limb; larger petal limbs to 1.5 cm across and 1.1 cm long, smaller limbs to 3 mm across and 5 mm long; claws range from 1.0 cm to 1.3 cm long and 2 mm to 4 mm wide about 2 mm from limb; adaxial limb with reddish purple jagged bar about 2 mm thick perpendicular to claw and rim of identical reddish purple or lighter 1 to 2 mm wide and occasional 1 to 2 mm inside limb perimeter; abaxial side uniform color except for some bleeding through from adaxial side.

*Color.*—Adaxial limb: reddish purple jagged bar and occasional perimeter closest to RHS 59A; margin and limb center between fuchsia pink RHS N74A and RHS N74B; abaxial.

*Limb.*—(Showing through from adaxial side) closest to RHS 74C; claw: between RHS 145B and RHS 145C both sides.

*Calyx.*—Glabrous, glaucous, five-toothed corolla tube fused in proximal 1.0 cm; about 1.7 cm long and 0.7 cm in diameter; RHS 146D with heavy anthocyanin tinting nearest RHS 187A.

*Peduncle.*—Glabrous, glaucous, terete, 22 cm long and 2 mm diameter; RHS N122A.

*Bracts.*—Two, opposite, broadly obtuse with acute apex, about 9 mm long and 8 mm wide; RHS 146D with heavy anthocyanin tinting nearest RHS 187A.

*Bracteoles.*—Two, opposite, broadly obtuse with acute apex, bases joined at stem; about 6 mm long and 3 mm wide; glaucous, RHS N138C at apex and center, lighter than RHS 1381) at base and margins.

*Stipules.*—None present.

*Androecium.*—Variable, stamens 0 to 18, filaments variable in length from 15 to 12 mm long, less than 1 mm diameter; pale green lighter than RHS 11D; anther oblong to 2.0 mm long and less than 1 mm wide, RHS 1584B; pollen rare, pollen color RHS 11D.

*Gynoecium.*—When present style split in two above ovary; pistil 1.7 cm long and about 1 mm diameter, white, lighter than RHS 69D except for distal 5 mm which are lighter than RHS N79B; stigma between RHS N79B.

*Ovary.*—Superior, spindle-shaped; 7 mm long and 3 mm wide; RHS 144C at distal end and nearest RHS 150D at proximal end.

Seed: Seeds have not been observed;

Comparison varieties: The new plant differs from the parents in the presence of reddish purple barring on the fuchsia pink petals. It has highly double flowers unlike the single flower of 'Red Dwarf' PP14437 (more commonly known as 'Eastern Star'); the most closely related cultivar is 'Cranberry Ice' PP18342 which is a single flower with wider perimeter reddish purple zone and has a less compact taller habit;

Disease resistance: The new plant is resistant to center die out from fungus or high temperatures. The plant grows best with adequate moisture and well-drained soil, but is able to tolerate high temperatures and some drought once established. Hardiness at least from USDA zone 4 through zone 9.

I claim:

1. A new and distinct cultivar of perennial Carnation or Pinks, *Dianthus* plant named 'Dragon Fruit' as herein described and illustrated, with fragrant highly double flowers, petals with a central fuchsia pink zone and reddish purple bar, tolerant of high temperatures, resistant to center die out and suitable as a garden ornamental, potted plant and for cut flower arrangements.

* * * * *